(12) United States Patent
Crombie

(10) Patent No.: US 6,909,021 B2
(45) Date of Patent: *Jun. 21, 2005

(54) METHOD OF EXTRACTING LUTEIN FROM GREEN PLANT MATERIALS

(75) Inventor: Lance B. Crombie, Northfield, MN (US)

(73) Assignee: Alfalfa America, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/770,345

(22) Filed: Feb. 2, 2004

(65) Prior Publication Data

US 2004/0220432 A1 Nov. 4, 2004

Related U.S. Application Data

(63) Continuation-in-part of application No. 10/400,968, filed on Mar. 27, 2003, now Pat. No. 6,737,552.

(51) Int. Cl.⁷ .............................................. C07C 35/21
(52) U.S. Cl. .................. 568/816; 554/11; 568/367; 585/351; 585/803; 585/833
(58) Field of Search .................... 568/816, 367; 554/11; 585/351, 803, 833

(56) References Cited

U.S. PATENT DOCUMENTS

| | | | | |
|---|---|---|---|---|
| 5,382,714 A | * | 1/1995 | Khachik | 568/834 |
| 5,591,343 A | * | 1/1997 | Kitaoka et al. | 210/634 |
| 5,789,647 A | * | 8/1998 | Heidlas et al. | 585/833 |
| 6,106,720 A | * | 8/2000 | Kanel et al. | 210/634 |
| 6,737,552 B1 | * | 5/2004 | Crombie | 568/816 |

OTHER PUBLICATIONS

Favati, J. Food Science, vol. 53, pp 1532–6 (1988).*

* cited by examiner

*Primary Examiner*—Michael L. Shippen
(74) *Attorney, Agent, or Firm*—Faegre & Benson LLP

(57) ABSTRACT

The present invention provides a method for extracting carotenoids from green plant materials using supercritical fluid extraction. A first and second supercritical fluid extraction is performed on the green plant composition at two different pressures to obtain two extracts. The first extract includes substantial amounts of β-carotene. The second extract may have a controlled concentration of β-carotene, and includes substantial amounts of lutein.

45 Claims, 2 Drawing Sheets

METHOD OF EXTRACTING LUTEIN FROM GREEN PLANT MATERIALS

CROSS-REFERENCE TO RELATED APPLICATION

This application is a continuation-in-part of U.S. application Ser. No. 10/400,968 filed Mar. 27, 2003, now U.S. Pat. No. 6,737,552, entitled "Method For Extracting Lutein From Green Plant Materials," which is hereby incorporated by reference.

BACKGROUND OF THE INVENTION

The present invention relates generally to the field of natural product extraction. More particularly, it concerns the use of supercritical fluid for the extraction of carotenoids from green plant materials.

Carotenoids are highly colored naturally occurring compounds, which are widely distributed in nature. Carotenoids may be classified as hydrocarbon carotenes or xanthophylls, which are oxygenated derivatives of carotenes. Representative examples of carotenes include β-carotene, alpha-carotene, and lycopene. Examples of xanthophylls include lutein, astaxanthin, canthaxanthin, zeaxanthin, and capsorubin. Carotenoids have been shown to have anti-oxidant properties and have been studied for the prevention of cancer and other human diseases.

Carotenoids are naturally present in edible leaves, flowers, and fruits, and are readily obtained from flowers (i.e. marigold), berries, and root tissue (i.e. carrots). Hydrocarbon carotenes, such as β-carotene and lycopene, are typically present in an uncombined free form, which is entrapped within chloroplast bodies within plant cells. Xanthophylls, such as lutein, are abundant in a number of yellow or orange fruits and vegetables such as peaches, mango, papaya, prunes, acorn squash, and oranges. Some Xanthophylls are present in plant flowers, such as marigolds, as long chain fatty esters, typically diesters, of acids such as palmitic and myristic acids. Generally, the free forms of carotenoids are present in the chloroplasts of green plants such as alfalfa, spinach, kale and leafy green plant materials. The free form of the carotinoids provides better adsorption when consumed in foods or as a supplement.

Lutein is a xanthophyll found in high concentrations in the macula of the eye and in the central part of the retina. It serves important roles in vision to help filter ultraviolet wavelengths of light to prevent damage to the eye lens and macula. Lutein's antioxidant properties are believed to help protect the macula, which is rich in polyunsaturated fats, from light-induced free radicals. Lutein can not be produced by the body, and consequently, must be ingested. Thus, lutein has become increasingly used in nutritional supplements for the prevention and/or treatment of vision losses due to macular degeneration, cataracts and retinitis pigmentosa.

Lutein has been shown to have significant potential in the prevention of age-related macular degeneration (AMD), the leading cause of irreversible blindness among Americans age 65 and older. Lutein helps build macular pigment density, a critical factor in the health of the macula and the retina. It has been found that high intake of lutein-rich green plants (spinach and kale) reduced the rate of AMD by 40% whereas Beta-carotene, vitamin A, zinc, and vitamin E were not seen to have an effect (Seddon et al. 1994). It has been shown that the accumulation of lutein in the macular pigment is dependent upon dietary intake and that the density of the macular pigment is related to the preservation of visual sensitivity and protection from AMD (Pratt, 1999, Richer, 2001). Other vision loss problems, such as cataracts and retinitis pigmentosa may also be stopped or reduced with a high intake of lutein.

The most common source of extracted lutein is from marigold flower petals, which contain one of the highest levels of lutein known and have a low concentration of other carotenoids. Methods of the purification of lutein-fatty acid esters from marigold flower petals are reported in U.S. Pat. Nos. 4,048,203, 5,382,714 and 5,648,564, in which dried ground marigold flower petals are extracted with a hydrocarbon solvent. In U.S. Pat. No. 5,648,564, extraction is performed 8–10 times with a 60-minute soak in hexane solvent for the extraction of the carotenoid from the marigold, and uses 320–400 L hexane for each 1 kg of dried marigold flower petals. The solvent is removed and the residue is dissolved in a hot alcohol. The solution is then filtered and then the lutein fatty acid ester is precipitated out. To obtain a more digestible form of lutein from extracted marigold flower petals, the extract is saponified at high pH (10+) or hydrolyzed to convert the product to a free form lutein.

U.S. Pat. No. 5,382,714, reports using commercially available saponified marigold oleoresins to crystallize lutein after saponification of the oleoresins using organic solvents. Purification of lutein from saponified marigold oleoresins without the use of added organic solvents is reported in U.S. Pat. No. 5,648,564.

There are several drawbacks to the extraction methods reported above. For example, the method reported in U.S. Pat. No. 5,648,564 uses caustic, high pH conditions that may be dangerous and may cause yield losses and vapor exposure, as well as producing toxic waste materials that need to be disposed of when completed. Trace amounts of these toxic chemicals and solvents may be present in the final products, which may be a problem for use of the resulting lutein extract for human consumption. The method reported in U.S. Pat. No. 5,382,714 uses organic and caustic solvents such as hexane, propane diol, and potassium hydroxide for extraction and saponification processes, which may not be totally removed during the purification process. Furthermore, neither method utilizes a starting material in which lutein is obtained in its free form. As previously noted, free form carotenoids such as lutein may provide better adsorption into the body during consumption. Thus, it would be desirable to provide a lutein extraction method that isolates the free form lutein without requiring the use of organic solvents during any steps, from the extraction of lutein from raw materials to the production of free lutein for consumption.

Lutein is abundantly present in a free, non-esterified form in green plants such as alfalfa, broccoli, green beans, green peas, lima beans, cabbage, kale, spinach, collards, mustard greens, turnip greens, kiwi, and honeydew. Green plants may also be rich in a variety of additional nutrients. For example, alfalfa is rich in proteins, minerals, and vitamins. It contains all 21 amino acids, and has significant concentrations of vitamins A, D, E, B-6, and K, calcium, magnesium, chlorophyll, linolenic and linoleic fatty acids, phytoestrogens, phosphorous, iron, potassium, trace minerals and several digestive enzymes. It also contains several saponins, many sterols, flavonoids, coumarins, alkaloids, acids, additional vitamins, amino acids, natural sugars, proteins (25% by weight), minerals, trace elements and other essential nutrients.

Extraction of lutein from green plants may be beneficial because it removes the need for the additional chemical step of saponification or ester cleavage to release the free lutein, which is the desired form for best absorption as consumed. However, the isolation and purification of lutein from plants has not been economical in the past because many expensive and time-consuming purification steps have been required to separate the lutein from the large quantities of other compounds present in the plant materials.

Supercritical fluids (SCF), which are gases above their critical pressure and temperature, have been used in certain industries to perform extractions. SCFs are dense gasses in a separate phase, which is distinct from normal gas phase. SCFs have a density and solvating power similar to that of a liquid and diffusion rates similar to that of a gas. Supercritical fluids are unlike liquids because their solvent power is highly sensitive to pressure changes and may be varied over wide limits by changing the pressure.

SCF extraction offers a relatively rapid, simple and inexpensive technique to perform purification or compound preparations. Most compounds, once dissolved, can quickly and cleanly be precipitated or removed from the supercritical fluids by lowering the pressure and/or temperature or both to achieve separation. Because a slight change in the pressure or temperature of a system causes significant change in solubility, the use of SCF enables a highly efficient isolation procedure of the desired components to be extracted. Using the method of post-extraction fractionation with a column designed to allow for temperature and pressure drops at different levels to gain the desired results may effect further concentration and purification.

One method of extracting carotenoids such as lutein from alfalfa without using toxic solvents is reported in Favati et al., Supercritical $CO_2$ Extraction of Carotene and Lutein from Leaf Protein Concentrates (1988). In the method reported in Favati, extracts containing mixtures of free lutein and $\beta$-carotene were obtained from alfalfa by supercritical extraction in a single stage extractor. This laboratory scale extraction was done in a single step, extracting a mixture of lutein, carotene, and other components from a leaf protein concentrate, with the relative concentrations of the two carotenoids dependent upon the extraction pressure used. The carotenoid content obtained from the process was 1.5% of the total extract.

Although the supercritical extraction method reported in Favati et al. overcomes the aforementioned problems with the health and safety risks of conventional solvent extractions, the resulting extracts include an uncontrolled mixture of lutein and other carotenoids in a single extraction. However, given the beneficial health effects of lutein, it would be desirable to obtain an isolated lutein extract containing a substantial concentration of lutein while being substantially free of other carotenoids. It may also be beneficial to obtain extracts with controlled concentrations of lutein and other desired nutrients such as $\beta$-carotene and/or fatty acids in order to treat patients with varying nutritional needs based on age (e.g., adults versus children) and/or the existence of eye conditions such as macular degeneration.

SUMMARY OF THE INVENTION

In one embodiment, the present invention provides a method for isolating lutein from green plant materials, in which a first supercritical fluid extraction of the green plant material is performed at a first pressure to obtain a first extract. A second supercritical fluid extraction of the green plant material is then performed at a second pressure to obtain a second extract. The second extract includes lutein, but is substantially free of carotenes such as $\beta$-carotene. The second extract is then separated from the supercritical fluid used to perform the first and second supercritical extractions. The first extract may be separated from the supercritical fluid in a similar manner.

A variety of green plant materials may be used as the starting material in the method of the present invention. Suitable green plant materials may include alfalfa, wheat grass, barley grass, broccoli, kale, spinach, cabbage, soybeans, green beans, mustard greens, turnip greens, collards, and green peas. In one embodiment, alfalfa is provided as the green plant material.

During the first and second supercritical extractions of the green plant material, the first and second pressures may be between about 8 MPa to about 200 MPa, more particularly between about 10 MPa to about 120 MPa. In one embodiment, the first pressure is lower than the second pressure. For example, the first pressure may be between about 10 and about 40 MPa, and the second pressure may be between about 41 and about 80 MPa. More particularly, the first pressure may be about 20 MPa and the second pressure may be about 65 MPa. The temperature during the supercritical extractions may be between about 31° C. to about 200° C., more particularly between about 31° C. to about 40° C., or even more particularly about 35° C. The temperature may be varied or remain constant during the extractions.

By optimizing the temperature and pressure at which the first and second supercritical extractions are performed, each extract may contain a substantial concentration of a particular substance, such as a desired carotenoid. In one embodiment, the first extract includes a substantial amount of $\beta$-carotene and the second extract includes a substantial amount of lutein, but is substantially free of $\beta$-carotene. In another embodiment, the first supercritical extraction is performed until the green plant material is substantially free of $\beta$-carotene. Additional extractions may also be performed at additional pressures and/or temperatures.

After performing the second supercritical extraction, the second extract may be separated from the supercritical fluid by lowering the pressure of the second extraction such that the lutein precipitates out of the second extract and onto a desired carrier. The first extraction may be separated in a similar manner. In one embodiment, the pressure of the first extract may be lowered to about 10 MPa and the pressure of the second extract may be lowered to about 40 MPa. The first and/or second extract may then be processed to form an end product suitable for consumption.

In another embodiment, the present invention provides a continuous method for obtaining a plurality of extracts from green plant material. A plurality of supercritical extractions may be performed at a plurality of pressures to obtain a plurality of extracts. For example, one of the extracts may contain substantial amounts of lutein. Another extract may contain substantial amounts of carotene. Other extracts may contain fatty acids, xanthophylls, zeaxanthin, astaxanthin, canthaxanthin, capsorubin and cryptoxanthin. Such extracts may be obtained by optimizing the pressure and/or temperature environment at which the extract is obtained to provide an extract having a substantial concentration of the desired substance.

In yet another embodiment, the present invention provides a method for obtaining lutein, in which a first supercritical extraction is performed at a first pressure and temperature to obtain a first extract. A second supercritical extraction is then performed at a second pressure and temperature to obtain a second extract. The second extract has a higher concentration of lutein than the first extract. The second extract may further include controlled concentrations of β-carotene and/or fatty acids.

In a further embodiment, the present invention provides a method for obtaining a plurality of extracts from green plant material. A first supercritical fluid extraction is performed at a first pressure and temperature to obtain a first extract. At least one additional supercritical fluid extraction is then performed at least one additional pressure and temperature. At least one of the additional extracts includes a higher concentration of lutein than the first extract. At least one of the additional extracts may also include a controlled mixture or combination of desired nutrients. For example, one of the plurality of extracts may include a mixture of lutein, carotene and/or fatty acids.

DETAILED DESCRIPTION

The present invention provides a method of extracting carotenoids such as lutein from green plant materials using a supercritical extraction process. The process is optimized as to the pressure and/or temperature during extraction to obtain the highest concentration of the desired carotenoids.

The green plant material utilized as the starting material for the supercritical fluid extraction may be derived from any suitable green plants, including alfalfa, wheat grass, barley grass, broccoli, kale, spinach, cabbage, soybeans, green beans, mustard greens, turnip greens, collards, or green peas. Although the green plants-may be utilized in any form (e.g. wet or dry) that includes and preserves the desired nutrients for supercritical extraction, a wet or dried chloroplast rich fraction of a green plant may be particularly useful for the extraction of carotenoids. The chloroplast rich fraction may be separated from other plant fractions by a process that includes the use of heat, acids, centrifugation, electrical field, or flocculants. The chloroplast rich fraction may be dried to 5–50% moisture with hot air, infrared heat, microwave radiation or a vacuum oven prior to the extraction with super critical fluid to preserve the desired components. Prior to supercritical fluid extraction, the chloroplast rich fraction may be washed with an aqueous solution. This washing step may remove bitter flavors from the chloroplast rich fraction to provide a more palatable fraction for use in a nutritional supplement. Alternatively, the starting material may be dried in such a manner that it preserves the desired nutrient(s) for subsequent supercritical extraction. Additionally, in this embodiment, the green plant material may be dried in the absence of oxygen if the desired nutrient is sensitive to oxidation by air or oxygen.

Pre-Extraction Processing of Green Plant Material

Figure 1:
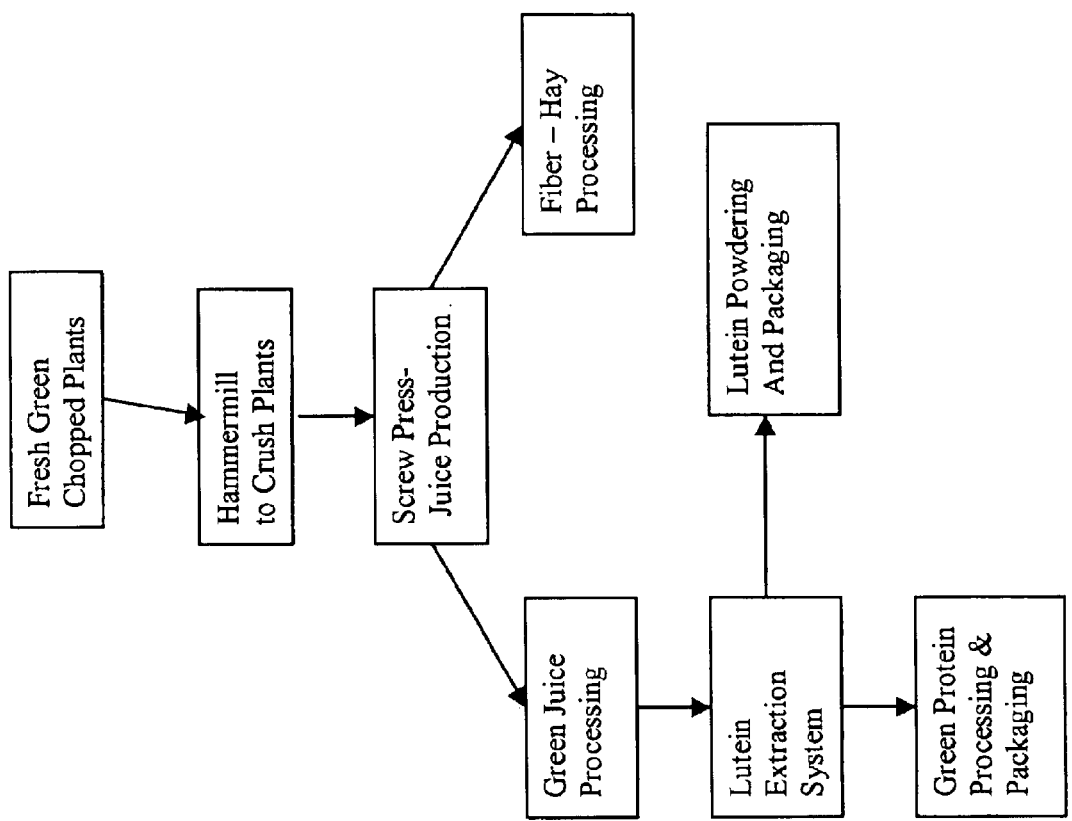
FIG. 1 illustrates a flow-chart for the fractionation and extraction of lutein according to an embodiment of the present invention.

The green plant material may be processed in a variety of ways prior to performing supercritical extraction to obtain a desired starting material. In one embodiment, the green plant material is subjected to the wet fractionation process illustrated in FIG. 1. In this embodiment, pre-bloom alfalfa may be harvested with standard farm equipment and then cut or chopped into ½ to 4-inch lengths. This cutting or chopping process is generally performed within 1 hour after harvesting to preserve the desired compounds. The cut or chopped alfalfa may then be crushed or macerated with rollers or with hammermill devices that ruptures the plant cell walls. The macerated green crop may then be squeezed in an appropriate pressing device, screw press, or other press that separates the green plant juices from the fibrous plant material.

The residue fibrous plant fraction, or wet fiber fraction of alfalfa typically possesses 55–65% moisture, 14–18% protein, and has most of the typical nutritional value of green forages. This fraction may be used for ruminant feed for beef or dairy cows in either wet or dry form.

The green plant juice is a mixture of cell sap materials, which include water, salts, chloroplasts, and cytoplasmic proteins, enzymes and cell compounds. The juice may be further treated by one of several methods to separate desired components. In one embodiment, the juice is typically subjected to heat coagulation at 60° C. for the chloroplast fraction and at 85° C. for the cytoplasmic fraction. Alternatively, the juice may be treated by acid precipitation, by density separations in centrifugal fields, or by direct electrical current fields. These techniques produce three general fractions: (a) a green protein chloroplast fraction; (b) a white cytoplasmic protein fraction; and (c) a brown juice fraction. In one embodiment, separation of the green protein concentrates from the brown juice is performed by centrifugation or filtration methods.

In one embodiment, the green protein chloroplast fraction of alfalfa is the starting green plant material for the supercritical extraction of lutein from green plants using supercritical fluid. This fraction is rich in plant chloroplasts and is typically composed of 50–55% protein on a dry weight basis and has 1.8 to 3.5 g xanthophylls per kg. The green chloroplast fraction may be used wet or may be dried prior to extraction of carotenoids. The dried form may produce a more stable material for extraction.

The fractions of the green plant juice may be dried under gentle conditions to preserve the desired components. Drying may be accomplished with hot air or other hot inert gases, infrared heat, microwave, vacuum oven devices, or any other method or combination of methods to remove water to the desired level.

Washing the green protein chloroplast fraction with an aqueous solution or water just prior to supercritical extraction may be advantageous. This washing process may remove off-flavors and bitter grassy flavors from the protein concentrate fraction and may make the extract more palatable for subsequent human consumption. Lutein has very little solubility in water, so the water wash causes only minor loss of product. This washing step may be particularly beneficial if the post-extraction green protein chloroplast fraction is used as part of a nutritional supplement.

Although alfalfa is used as the green plant material in the reported embodiment, any fresh green crop that can be processed by wet fractionation may be used, including wheat grass, barley grass, broccoli, kale, spinach, cabbage, soybeans, green beans, mustard greens, turnip greens, collards, or green peas. For example, the wet fractionation process reported above may be easily adapted to wheat grass and barley grass. Since the wet fractionation is similar for alfalfa and grasses the process is the same for most fresh green plants.

Supercritical Extraction Process

Once a suitable green plant material is obtained, supercritical extraction may be performed by passing supercritical fluids (SCF) through the green plant material. The supercritical fluid used in the method of the present invention may include $CO_2$, $CH_2CH_2$, $CH_3CH_3$, $N_2O$ or other suitable supercritical fluids. A co-solvent may be used along with the supercritical fluid to increase the solvation power for polar analytes that do not readily dissolve in supercritical fluids. Co-solvents are often referred to as entrainers or modifiers, and are typically a liquid organic solvent such as methanol, ethanol, propylene carbonate, acetone, tetrahydrofuran, formic acid, propylene glycol, or ethyl acetate that are blended with the carbon dioxide. With an entrainer, the solvent system has a much higher polarity and is able to solubilize more polar analytes for extraction. Entrainers have been shown to substantially increase the solubility of zeaxanthin in supercritical carbon dioxide as reported, in part, in U.S. Pat. No. 5,747,544. In one embodiment, the SCF includes ethanol as an entrainer at 1–5% concentration in the extracted material. This entrainer may produce a better extraction at lower pressures.

In one embodiment, the SCF is carbon dioxide, which has a critical pressure of 1070 psi (about 7.4 MPa) and a critical temperature of 31° C. Solvation power increases as pressure and temperature is raised above the critical pressure and temperature. Supercritical $CO_2$ may be manipulated at room temperature, making the handling of heat-vulnerable substances easy and safe. Fire and explosion hazards associated with large-scale extractions using organic solvents are eliminated with this solvent.

In practice, the fluid is passed through the green plant materials inside an extraction vessel. The fluid diffuses into the pores of the green plant material matrix, solubilizes the extracts (e.g., lutein or carotene) of interest, and then carries the extracts away from the green plant matrix in a solution. The extract is then collected, and the green plant matrix (now without the extract) is left behind in the extraction vessel. Supercritical fluids have favorable diffusion and viscosity coefficients providing for good mass transfer characteristics. Changing fluid pressure or temperature may control solvent strength in a precisely controlled manner. As opposed to conventional solvent extraction, any residual $CO_2$ left in the extract after separation is inert and non-toxic, such that human consumption of the material is not harmful.

Figure 2:
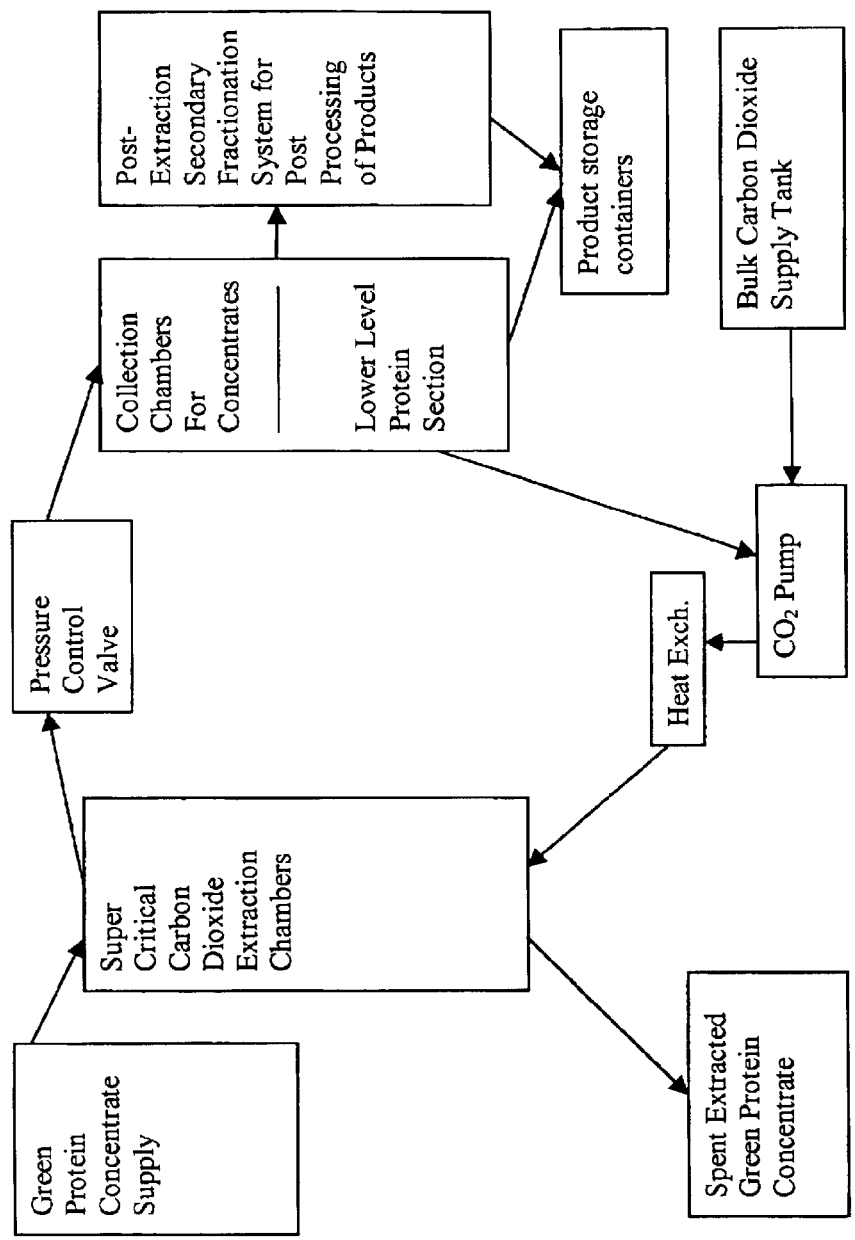
FIG. 2 illustrates a lutein extraction chamber and a process flow diagram with collection system according to an embodiment of the present invention.

The extraction process illustrated in FIG. 2 is typically performed in a round thick-walled very high-pressure chamber, engineered to withstand pressures up to about 120 MPa (1450–17,400 psi), more particularly up to about 70 MPa (10,150 psi). The chamber has openings for adding a suitable charge of green plant protein concentrate at the top and for removal of the charge after extraction at the bottom. Appropriate pipes and pump systems direct the supercritical carbon dioxide fluid into the bottom of the chamber such that the liquid will flow up through the bed of green plant material and to the top of the chamber for delivery to a collection device. During or after delivery of the extract to the collection device, the supercritical fluid may be depressurized to below the desired pressure to collect the desired extract. In one embodiment, the extraction method is performed by counterflowing the SCF relative to the movement of the green plant material.

Importantly, the temperature and pressure may be controlled with conventional devices such as conventional pumps, valves and/or heat exchangers before, during and/or after extraction to optimize the concentration, combination or mixture of lutein or other nutrients in a particular extraction. After leaving the extraction chamber, a pressure reduction valve may be positioned prior to the collection device intake to effect release or precipitation of the desired extract alone, or onto a specific carrier material in the collection device. A double valve at the bottom of the collection device allows for periodic removal of the extract (with or without the carrier). The vented carbon dioxide liquid from the top of the collection device at a reduced pressure may then be recycled to a filter system and recompressed to high pressure for use in a second extraction function in the extraction vessel. Extraction is continued until an appropriate degree of desired product is isolated from the plant material being processed. The volume of SCF needed for the desired extraction depends on the pressure and temperature used for each product obtained. Typically 5–50 cubic feet of SCF are needed for each cubic foot of plant concentrate extracted. The ratio between the volume of supercritical fluid and green plant material may be referred to as the solvent to feed ratio, and may more particularly range from 10:1 to 50:1.

In one embodiment, the supercritical extraction is performed under at least two different pressure and temperature conditions within the extraction chamber. At a first pressure and temperature, a first extract containing substantial amounts of carotene may be obtained. At a second pressure and temperature, a second extract containing substantial amounts of lutein is obtained. In one embodiment the second extract may be substantially free of β-carotene. For example, the second extract may have less than 10 percent β-carotene, more particularly less than 5 percent. This may be accomplished by performing the first extraction until the green plant material is substantially free of β-carotene, and then subsequently performing the second extraction until the desired lutein extraction is completed. In one example, the first extraction may be performed at a pressure of between about 10 and about 40 MPa, more particularly between about 15 and about 35 MPa. The second extraction may be performed at a pressure of between about 41 and about 80 MPa, more particularly between about 55 and about 80 MPa. Both extractions may be performed at between about 31° C. and about 100° C. The extractions may be performed at the same or different temperatures. For example, the first extraction temperature may range from between about 31° C. to about 40° C. The second extraction temperature may range from between about 65° C. to about 75° C. depending, at least in part, upon the extraction pressure, the green plant material, the supercritical fluid volume and/or whether a co-solvent entrainer is employed.

As is evident from the foregoing, the second supercritical fluid extraction (or other additional extractions) does not necessarily have to be performed at both a different temperature and a different pressure than the first extraction. Rather, one or both of the temperature and pressure may be changed between extractions to achieve the desired result. Thus, as used herein, changes to the "pressure and temperature," or "pressure and temperature conditions" refers to changes in the overall condition under which the extraction is preformed, rather than to changes in both the temperature and pressure.

In an alternate embodiment, multiple extractions may be performed at multiple pressures and temperatures to obtain extracts containing concentrations of a desired nutrient or nutrients that are different than the concentrations of the nutrient or nutrients that may be obtained by merely performing a single extraction. For example, a first extraction may be performed at a first pressure to obtain a first extract. A second extraction may then be performed at a second pressure and temperature to obtain a second extract. The first extract may contain a substantial concentration of β-carotene, while the second extract may contain a higher concentration of lutein than the first extract, while also optionally including a controlled amount of β-carotene and/or fatty acid. Similar multiple extraction methods may be used to achieve a desired concentration (or concentration range) of a mixture of nutrients in a particular extract that could not be obtained by utilizing a single extract of the green plant material.

In this manner, an extraction may be obtained having a controlled combination of lutein, β-carotene and/or fatty acids. This may be beneficial for certain applications, because it has been recognized that β-carotene and lutein are important in preserving eye health in that the lutein is concentrated in the macula and β-carotene is converted to Vitamin A, which is critical to night vision and overall retinal health. Furthermore, fatty acids may improve the sorption of the lutein and β-carotene. Thus, a blended mixture of β-carotene and lutein with a suitable concentration of fatty acids is a good nutritional supplement for maintaining and/or improving eye health.

In one embodiment, the desired extract may include high concentrations of lutein, with only trace amounts of β-carotene and fatty acids. In another embodiment, the desired extract may include a controlled concentration of β-carotene, lutein and fatty acids. For example, the extract may include between about 10 and 90 weight percent, more particularly about 40 and about 60 weight percent lutein, between about 10 and 90 weight percent, more particularly about 40 and about 60 weight percent β-carotene, and between about 5 and 20 weight percent fatty acids.

Additionally, the supercritical extraction process of embodiments of the present invention may be used to remove other undesired materials, including chlorophyll, flavor and odor-producing compounds, and hormones such as coumesterol. Thus, in one embodiment, at least one extract includes lutein, but is substantially free of hormones such as coumesterol, odor and flavor producing compounds and/or chlorophyll.

Although the pressure, temperature and volume at which the supercritical extractions are performed are related, each of these variables or conditions may be independently adjusted and/or optimized to produce one or more extracts having specific concentrations of desired nutrients and/or other substituents. As an example, if a total separation of β-carotene is desired from alfalfa, an initial supercritical fluid extraction under low temperature and/or low pressure (32° C.; 20 MPa; 20–50 volumes of $CO_2$) may be performed such that substantial portions of β-carotene will be isolated and concentrated in the extract. If higher temperatures and/or higher pressures (43° C.; 50 MPa; 20–30 volumes) are used, the lutein and β-carotene may be concentrated in a single extract.

Furthermore, the volume of supercritical fluid needed to extract the desired nutrient(s) may depend on the pressure and temperature at which the extraction is performed. For example, under low temperature and pressure conditions, it may be desirable to use a greater volume of supercritical fluid to obtain the desired extract. However, under higher temperature and pressure conditions, a lower volume of supercritical fluid may be required to obtain a desired extract. In this manner, it is possible to adjust or optimize the extraction pressure, temperature and/or volume to obtain extractions having the desired type, concentration and/or purity of nutrients.

In certain embodiments, it may be desirable to perform at least a third extract at a third temperature or pressure. For example, saponins may be isolated and extracted under higher pressure and/or temperature conditions than lutein and β-carotene.

Post-Extraction Processing

Optionally, after separation, the extract may be further processed to produce a desired end product. For example, a secondary column fractionation step may be used to further concentrate and purify lutein or β-carotene. Additionally, the first or second extract may be purified with simple non-toxic solvents such as food grade ethanol, a vegetable oil, or water to provide a substance that is crystalline and essentially pure and free of any potentially toxic chemicals, even on a trace level. Typically, the lutein is concentrated to 5–50% concentration in oils or dry form for bulk markets. In one embodiment, the first and second extracts are combined before or after separation in order to provide an end product having a controlled concentration of carotene and lutein. Advantageously, in embodiments that utilize multiple extractions to obtain a controlled concentration of carotene and lutein (or other nutrients), this post-extraction processing may be curtailed or completely eliminated.

The lutein and/or β-carotene may be also further processed by blending or milling with a suitable base material (e.g. green plant protein concentrate or other blending agents) to form an end product suitable for human consumption. This blending or milling step may take place in the collection device wherein the extract is precipitated into the base material. The double valve at the bottom of the collection device may then be actuated to release the blended extract. In this manner, protein concentrates or blending agents may be used as a sorption agent in the lower pressure collection vessels.

End Products

The extract may be combined with a suitable carrier to form an end product. The end product may be a powder, an agglomerated powder or a solution in edible oil that includes the extract. A protein matrix or beadlets may be produced to protect the extract from deterioration or oxidation. It may be analyzed for specific carotenoid content and then mixed with alfalfa or plant based natural fillers, sugars, gelatins, or starches to form a desired standardized dry product. In one embodiment, the extract is combined with a green chloroplast rich fraction of alfalfa (which may also be used as the starting green plant material) such that an end product will contain only a single source ingredient and may be labeled as 100% alfalfa based. The use of the green chloroplast fraction of alfalfa as the carrier in the final product is nutritionally beneficial because of the high content of useful proteins, vitamins, amino acids, chlorophyll and other compounds in the fraction in addition to the presence of the concentrated lutein. Furthermore, the end product is then derived from a single source plant product, without additional fillers or additives.

The invention is further described in the Example below.

EXAMPLE

Fresh field chopped alfalfa was run through a hammermill to rupture plant cells. The tip speed of the hammers was set at 15,000 feet per minute to crush the green wet (80% moisture) material without causing the material to be pulped or broken into smaller pieces. The crushed material was run through a single (6") screw press (Model Number VP6, available from Vincent Corp., Tampa, Fla.) such that the outlet restriction (set at 25 psi) produced high continuous pressure to effect separation of green plant juices from the plant fibers. The long barrel screw has a fine barrel screen to allow juice to flow from the fiber. The ratio of juice to fiber was about 1:1, however, the yield of juice to fiber will be less if the starting material is old or more matured, or if it is naturally dryer than lush pre-bloom growing alfalfa. The juice was adjusted to a pH of 8.0 with ammonia water, and immediately heated from ambient temperature with a double boiler system with a propane burner such that the juice was heated within 5–10 minutes after production to between 82–85° C. to cause heat coagulation of the green and white (cytoplasmic) proteins. The green protein coagulum was separated with a weir type screen to separate the green "curd" from the brown waste plant juices.

The green wet protein "curd" (i.e. the green plant material) was immediately dried in a continuous perforated temperature controlled zone dryer such that limited heat (below 85° C.) with limited air at 5–10% relative humidity produced a dry granular material. The wet protein curd started at approximately 75% moisture and was dried to 8% moisture. This material was then extracted or stored in oxygen-excluding bags or containers in the dark at room temperature until extracted.

The green plant material was then transferred to a very high pressure extraction chamber (about 5 cm×50 cm) having round thick-walls, and being engineered to withstand pressures of up to about 70 MPa (10,150 psi). The chamber was brought up to pressure and temperature with 20 MPa carbon dioxide fluid at 30° C. The temperature and pressure of the SCF stream with an injected 3% liquid ethanol (vol./vol.) entrainer was regulated by a high pressure carbon dioxide pump and heat exchanger controlled with water in a tube and shell system. This extraction continued until the beta-carotene (about 27 bed volumes) was removed as measured in side port sampling at the top of the column outlet line. The pressure was then increased to 65 MPa to extract the lutein from the green plant material with about 20 bed volumes.

The desired compounds were collected after extraction into a small but tall (1 meter) tower with reduced pressure through reducing valves such that the beta-carotene and lutein fractions were collected into chambers with dried green protein powder at 10 MPa and 40 MPa respectively. The lower ¼ of the collection vessel has large valves to allow the desired fractions to fall out into the protein fractions such that after the separation of the fractions, the lower collection chamber was sealed off and the pressure released to remove the end products.

The yield in this example was 2.6 grams beta-carotene and 2.4 grams of lutein per kilogram of dry (6% moisture) starting material. The products were tested for purity without the blending with the green protein fraction with silica gel HPLC columns and were 80% and 72% pure carotene and lutein respectively. The drying of the green protein is critical in preserving the desired end products since the dried materials ranged from 0.6 to 3.4 grams of each carotenoid as measured with high performance liquid chromatography (HPLC) with known pure standards (available from Sigma Chemical, St. Louis, Mo.).

What is claimed is:

1. A method for obtaining lutein from green plant materials comprising:
    performing a first supercritical fluid extraction of a green plant material at a first pressure and temperature to obtain a first extract;
    performing a second supercritical fluid extraction of the green plant material at a second pressure and temperature to obtain a second extract that includes a higher concentration of lutein than the concentration of lutein in the first extract, and
    separating the second extract from the supercritical fluid.

2. The method of claim 1 wherein the green plant material is derived from dried green plants or green plant fractions.

3. The method of claim 1 wherein the first extract comprises β-carotene, at least one fatty acid, or both.

4. The method of claim 1 wherein the first supercritical fluid extraction is performed to reduce the concentration of β-carotene, fatty acid, or both in the green plant material.

5. The method of claim 1 wherein the first supercritical fluid extraction is performed to reduce the concentration of coumesterol in the green plant material.

6. The method of claim 1 wherein the first supercritical fluid extraction is performed to reduce the concentration of chlorophyll in the green plant material.

7. The method of claim 1 wherein the first supercritical fluid extraction is performed to reduce the concentration of odor or flavor-producing compounds in the green plant material.

8. The method of claim 1 wherein the second extract comprises β-carotene.

9. The method of claim 1 wherein the second extract comprises between about 10 and about 60 weight percent β-carotene.

10. The method of claim 1 wherein the concentration of β-carotene in the second extract is less than in the first extract.

11. The method of claim 1 wherein the second extract comprises at least one fatty acid.

12. The method of claim 11 wherein the second abstract comprises less than about 20 weight percent fatty acid.

13. The method of claim 1 wherein the second extract is free of hormones.

14. The method of claim 1 wherein the second extract is free of coumesterol.

15. The method of claim 1 wherein the second extract is substantially free of chlorophyll.

16. The method of claim 1 wherein the first and second pressures are between about 10 and about 120 MPa.

17. The method of claim 1 wherein the first pressure is lower than the second pressure.

18. The method of claim 1 wherein the first pressure is between about 10 and about 40 MPa.

19. The method of claim 1 wherein the second pressure is between about 41 and about 80 MPa.

20. The method of claim 1 wherein the first pressure is between about 15 and about 35 MPa and the second pressure is between about 55 and about 80 MPa.

21. The method of claim 1 wherein the first and second supercritical fluid extractions occur at between about 31° C. and about 100° C.

22. The method of claim 1 wherein the first temperature is lower than the second temperature.

23. The method of claim 1 wherein the first temperature is between about 31° C. and about 40° C., and the second temperature is between about 65° C. and about 75° C.

24. The method of claim 1 wherein the first and second supercritical fluid extractions occur at a substantially constant temperature.

25. The method of claim 1 wherein separating the second extract from the supercritical fluid comprises subjecting the second extract to a post-extraction pressure that is lower than the second pressure.

26. The method of claim 25 wherein the post-extraction pressure is between about 15 and about 45 MPa.

27. The method of claim 1 further comprising separating the first extract from the supercritical fluid.

28. The method of claim 27 comprising separating the first extract from the supercritical fluid by subjecting the first extract to a post-extraction pressure that is lower than the first pressure.

29. The method of claim 27 comprising combining the first and second extract.

30. The method of claim 1 comprising performing at least a third supercritical fluid extraction of the green plant material at a third pressure and temperature to obtain at least a third extract.

31. The method of claim 30 wherein the third pressure is lower or higher than the first and second pressures.

32. The method of claim 30 wherein the third pressure is higher than the first and second pressures.

33. The method of claim 30 wherein third extract comprises at least one saponin.

34. A method for obtaining a plurality of extracts from green plant material comprising performing a first supercritical fluid extraction of the green plant material at a first pressure and temperature to obtain a first extract;

performing at least one additional supercritical fluid extraction of the green plant material at least one additional pressure and temperature to obtain at least one additional extract, wherein at least one of the additional extracts includes a higher concentration of lutein than in the first extract; and separating at least one of the additional extracts from the supercritical fluid.

35. The method of claim 34 wherein at least one extract comprises β-carotene.

36. The method of claim 34 wherein at least one extract comprises alpha-carotene.

37. The method of claim 23 wherein at least one extract comprises at least one fatty acid.

38. The method of claim 37 wherein the green plant material is derived from alfalfa, and the fatty acid comprising linolenic acid, linoleic acid palmitic acid or oleic acid.

39. The method of claim 34, wherein at least one extract comprises xanthophyll, zeaxanthin, astaxanthin, canthaxanthin, capsorubin, or cryptoxanthin.

40. The method of claim 34 wherein at least one of the extracts comprises coumesterol.

41. The method of claim 34 wherein at least one extract comprises a mixture of at least two nutrients.

42. The method of claim 34 wherein at least one of the additional extracts comprises a mixture of lutein and β-carotene.

43. The method of claim 43 wherein the additional extract comprises between about 20 and about 60 weight percent lutein and between about 20 and about 60 weight percent β-carotene.

44. The method of claim 42 wherein the additional extract further comprises at least one fatty acid.

45. The method of claim 44 further comprising between about 5 and about 20 weight percent of at least one fatty acid.

* * * * *

UNITED STATES PATENT AND TRADEMARK OFFICE
CERTIFICATE OF CORRECTION

| | | |
|---|---|---|
| PATENT NO. | : 6,909,021 B2 | Page 1 of 1 |
| APPLICATION NO. | : 10/770345 | |
| DATED | : June 21, 2005 | |
| INVENTOR(S) | : Lance B. Crombie | |

It is certified that error appears in the above-identified patent and that said Letters Patent is hereby corrected as shown below:

Column 12, line 20, delete "loss" and insert therefor --less--

Column 14, line 4, delete "comprising" and insert therefor --comprises--

Column 14, line 5, after "linolenic acid" insert therefor --,--

Column 14, line 17, delete "43" and insert therefor --42--

Signed and Sealed this

Fifth Day of May, 2009

JOHN DOLL
*Acting Director of the United States Patent and Trademark Office*